United States Patent [19]
Larsen et al.

[11] Patent Number: 5,529,067
[45] Date of Patent: Jun. 25, 1996

[54] METHODS FOR PROCEDURES RELATED TO THE ELECTROPHYSIOLOGY OF THE HEART

[75] Inventors: Charles E. Larsen, Cumming; Roel Trip, Snellville; Cheryl R. Johnson, Atlanta, all of Ga.

[73] Assignee: Novoste Corporation, Norcross, Ga.

[21] Appl. No.: 294,478

[22] Filed: Aug. 19, 1994

[51] Int. Cl.⁶ .......................... A61B 5/042; A61B 17/36; A61N 5/02
[52] U.S. Cl. .............................. 128/642; 606/21; 606/29; 606/33; 606/41; 607/101; 607/113; 607/122
[58] Field of Search .............................. 128/642; 606/20, 606/21, 28, 29, 41, 33; 607/99–102, 113, 119, 122

[56] References Cited

U.S. PATENT DOCUMENTS

| | | |
|---|---|---|
| Re. 32,204 | 7/1986 | Halvorsen et al. . |
| 4,641,649 | 2/1987 | Walinsky et al. . |
| 4,860,744 | 8/1989 | Johnson et al. . |
| 4,887,608 | 12/1989 | Mohl et al. . |
| 4,898,169 | 2/1990 | Norman et al. . |
| 4,934,996 | 6/1990 | Mohl et al. . |
| 4,969,470 | 11/1990 | Mohl et al. . |
| 5,122,137 | 6/1992 | Lennox et al. . |
| 5,131,397 | 7/1992 | Crowley et al. . |
| 5,139,496 | 8/1992 | Hed ............................................. 606/21 |
| 5,147,355 | 9/1992 | Friedman et al. . |
| 5,207,674 | 5/1993 | Hamilton ................... 606/21 |
| 5,228,442 | 7/1993 | Imran . |
| 5,231,995 | 8/1993 | Desai . |
| 5,237,996 | 8/1993 | Waldman et al. . |
| 5,255,679 | 10/1993 | Imran . |
| 5,281,213 | 1/1994 | Milder ...................... 606/21 |
| 5,304,214 | 4/1994 | DeFord . |
| 5,309,910 | 5/1994 | Edwards et al. . |
| 5,334,193 | 8/1994 | Nardella . |
| 5,339,193 | 8/1994 | Korpert et al. . |
| 5,348,554 | 9/1995 | Imran et al. . |

OTHER PUBLICATIONS

Hariman et al., "Cryothermal Mapping of the Sinus Node in Dogs: A Simple Method of Localizing Dominant and Latent Pacemakers," *Cardiovascular Research*, 23, 231–238, 1989.
Gessman et al., "Localization and Mechanism of Ventricular Tachycardia by Ice Mapping 1 Week After the Onset of Myocardial Infarction in Dogs," *Circulation* 68, No. 3, 657–666, Sep. 1983.
Gessman et al., "Dissociation of the Site of Origin from the Site of Cryo–termination of Ventricular Tachycardia," *Pace*, vol. 6, pp. 1293–1305, Nov.–Dec. 1983.

*Primary Examiner*—Lee S. Cohen
*Attorney, Agent, or Firm*—Cook, McFarron & Manzo, Ltd.

[57] ABSTRACT

Methods and apparatus are disclosed for use in procedures related to the electrophysiology of the heart, such as identifying or evaluating the electrical activity of the heart, diagnosing and/or treating conditions associated with the electrophysiology of the heart. An apparatus having thermocouple elements of different electromotive potential conductively connected at a junction is introduced into the interior of the heart and a section of heart tissue is contacted with the junction. An electrical current is passed through the thermocouple elements to reduce the temperature of the junction in accordance with the Peltier effect and thereby cool the contacted heart tissue. The effect of the cooling may be monitored and, if desired, the section of heart tissue may be treated.

26 Claims, 5 Drawing Sheets

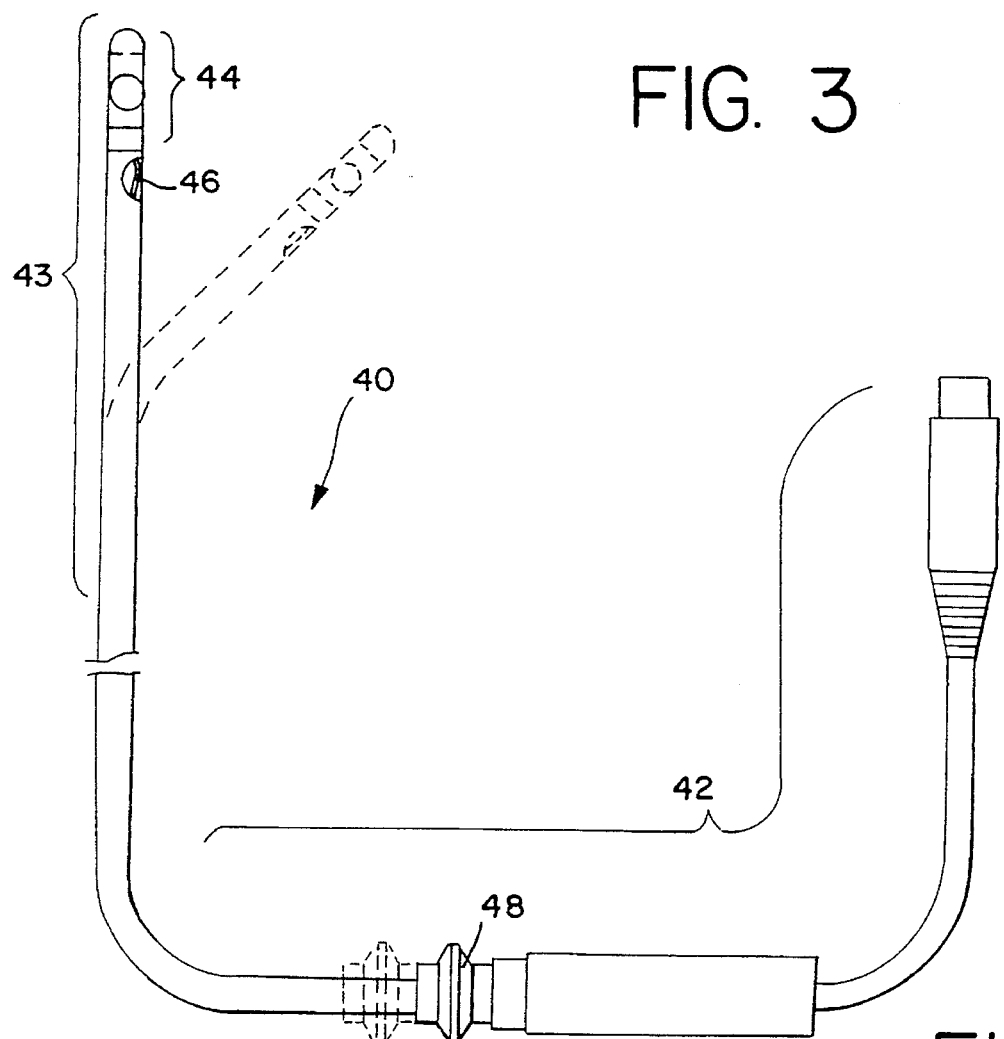

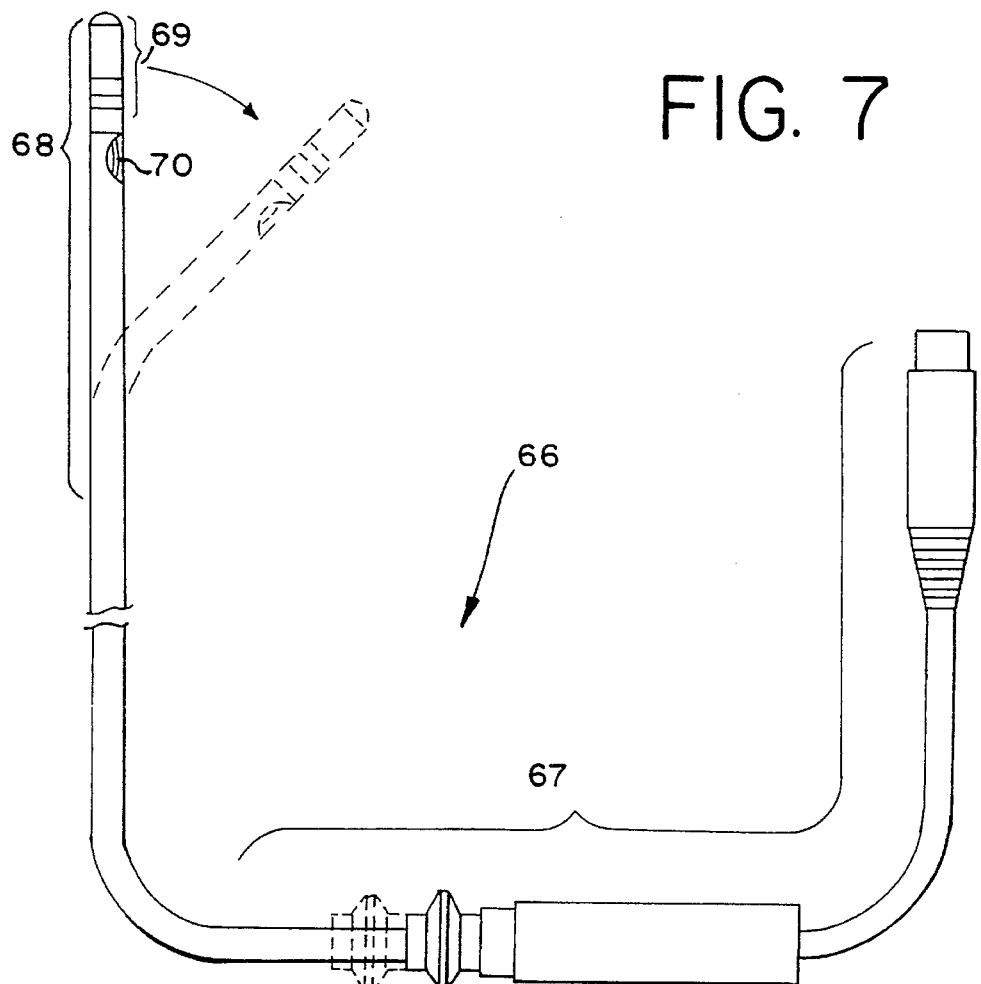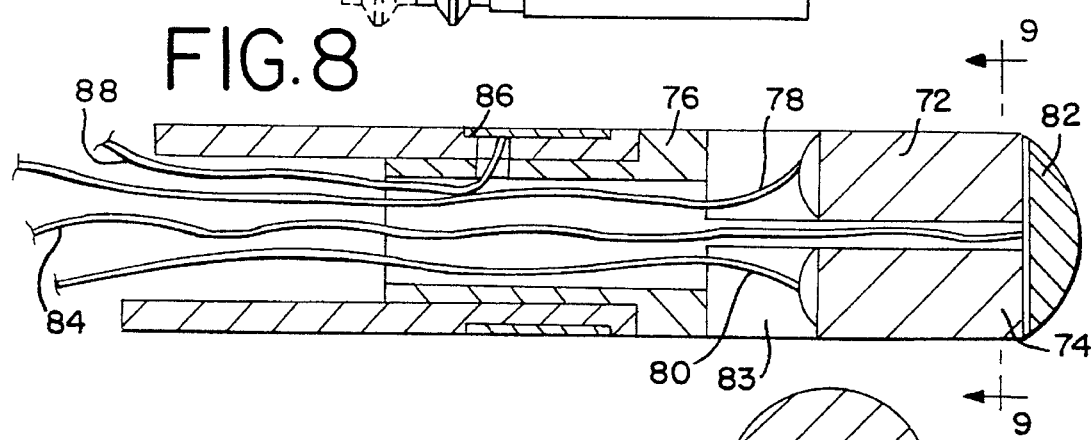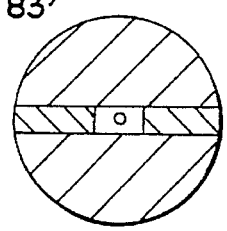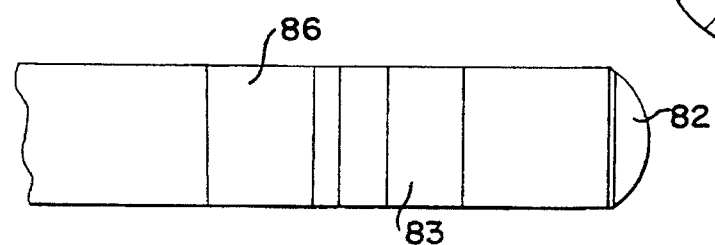

5,529,067

METHODS FOR PROCEDURES RELATED TO THE ELECTROPHYSIOLOGY OF THE HEART

FIELD OF THE INVENTION

The present invention relates generally to methods and apparatus for diagnosing or treating electrophysiological conditions of the heart. More specifically, the present invention relates to novel methods and apparatus for evaluating the electrical activity of the heart, for identifying an electrophysiological source of heart arrhythmia, and for treating heart arrhythmia.

BACKGROUND ART

As is well known, the human heart has four chambers for receiving blood and for pumping it to various parts of the body. In particular, the two upper chambers of the heart are called atriums, and the two lower chambers are called ventricles.

During normal operation of the heart, oxygen-poor blood returning from the body enters the upper right chamber known as the right atrium through the superior vena cava and inferior vena cava. The right atrium fills with blood and eventually contracts to expel the blood through the tricuspid valve to the lower right chamber known as the right ventricle. Contraction of the right ventricle ejects the blood in a pulse-like manner from the right ventricle to the pulmonary artery which divides into two branches, one going to each lung. As the oxygen-poor blood travels through the lungs, it becomes oxygenated (i.e. oxygen-rich).

The oxygenated blood leaves the lungs through the pulmonary veins and fills the upper left chamber of the heart known as the left atrium. When the left atrium contracts, it sends the blood through the mitral valve to the lower left chamber called the left ventricle. Contraction of the left ventricle, which is the stronger of the two lower chambers, forces blood through the main artery of the vascular system known as the aorta. The aorta branches into many smaller arteries and blood vessels that eventually deliver the oxygen-rich blood to the rest of the body.

As is apparent from the description above, the proper sequence of contraction and relaxation of the heart chambers is fundamental to its operation. Contraction of the heart chambers is controlled by the heart's conduction system, which includes areas of specialized "nodal" tissue or "nodes" capable of generating and transmitting electrical impulses. The ability to generate electrical impulses is known as "automaticity."

The natural pacemaker of the heart is called the SA (sino-atrial) node. It lies in the groove where the superior vena cava joins the right atrium. The SA node contains two types of cells, one of which exhibits automaticity.

In general, the conduction of an electrical impulse generated by the SA node proceeds as follows. The cardiac impulse travels across the walls of the atria, eventually causing the atria to contract. The impulses generated by the SA node are also transmitted to the atrio-ventricular (AV) node located in the lower portion of the right atrium near the right ventricle. From the AV node, the impulses travel through another area of nodal tissue known as the bundle of His and eventually to the Purkinje's fibers that envelop the ventricles. When the impulses reach these fibers, they cause the ventricles to contract.

More specifically, from the SA node the cardiac impulse spreads radially along ordinary atrial myocardial fibers. A special pathway, the anterior interatrial myocardial band, conducts the impulse from the SA node directly to the left atrium. In addition, three tracts, the anterior, middle, and posterior internodal tracts or pathways constitute the principal routes for conduction of the cardiac impulse from the SA to the AV node. These tracts consist of ordinary myocardial cells and specialized conducting fibers.

The AV node is situated posteriorly on the right side of the muscle wall dividing the heart's right and left atria, (known as the interatrial septum). The AV node also contains cells that exhibit automaticity. The AV node receives and relays the impulses through the septum to a cluster of fibers between the ventricles known as the bundle of His.

The bundle of His passes down the right side of the inter ventricular septum (the muscle wall between the right and left ventricles) and then divides into the right and left bundle branches. The right bundle branch is a direct continuation of the bundle of His and it proceeds down the right side of the interventricular septum. The left bundle branch, which is considerably thicker than the right, branches almost perpendicularly from the bundle of His and bisects the interventricular septum. On the surface of the left side of the interventricular septum the main left bundle branch splits into a thin anterior division and a thick posterior division.

The right bundle branch and the two divisions of the left bundle branch ultimately subdivide into a complex network of conducting fibers called Purkinje's fibers which envelop the ventricles.

As an impulse travels from the region of the atria to the ventricles, the first portions of the ventricles to be excited are the interventricular septum and the papillary muscles. The wave of activation spreads to the septum from both its left and its right endocardial surfaces (the inner membrane of the heart wall). Early contraction of the septum tends to make it more rigid and allows it to serve as an anchor point for the contraction of the remaining ventricular myocardium (the middle layer of muscle that comprises the heart wall).

The endocardial surfaces of both ventricles are activated rapidly, but the wave of excitation spreads from endocardium to the outer membrane or sheath of the heart wall known as the epicardium at a slower velocity. Because the right ventricular wall is appreciably thinner than the left, the epicardial surface of the right ventricle is activated earlier than that of the left ventricle. The last portions of the ventricles to be excited are the posterior basal epicardial regions and a small zone in the basal portion of the interventricular septum.

Cardiac arrhythmia refers to a disturbance in the rhythm of contraction and relaxation of the heart's chambers. In cardiac arrhythmia, the atria and/or ventricles do not contract and relax in the regular and sequential pattern described above, and may instead contract prematurely and/or randomly. In the most serious types of arrhythmia, such as fibrillation, the impulses may fragment into multiple, irregular circuits which are incapable of causing coordinated contractions of the heart chamber and, therefore, may adversely affect the pumping of blood.

Various causes of arrhythmia have been identified. One cause of cardiac arrhythmia may be a disorder in the formation of the impulse. For example, although the primary source of impulse formation is the SA node, it is known that most cardiac cells are capable of exhibiting automaticity. If an impulse traveling, for example, from the SA node is delayed or diverted, other cardiac cells or clusters of cells outside the areas of nodal tissue may spontaneously initiate an impulse. These cells or cell clusters are known as ectopic foci. The impulses generated by ectopic foci may be transmitted to the atria and/or ventricles prior to the impulse that is traveling along the normal conductive pathway, thereby causing premature contraction of the heart chamber.

Arrhythmia may also be caused by disorders in the conduction or transmission of an impulse from one region of the heart to another region. In this case, injury to a section of the heart tissue that is part of the normal conductive pathway may slow, block or even divert transmission of the impulse from its normal path. Impulses traveling along a different pathway proximal to the blocked pathway may attempt to reenter the blocked pathway. If the impulse reenters the blocked pathway, it may prematurely stimulate other nodal tissue causing the atria or ventricles to contract before these chambers have returned to their relaxed state.

One known method of treating cardiac arrhythmia, includes ablating the focal point of the arrhythmia within the heart tissue with the tip of a catheter or other surgical device. The devices used for treating arrhythmia typically have elongated, small diameter tubular bodies that include tips that can be heated, super-cooled or are capable of emitting radiofrequency energy. Typically, the device is introduced and advanced through the vascular system of the patient until the tip of the device reaches the desired location (e.g. the suspected source of the arrhythmia for treatment). When applied to the source of the arrhythmia, these heated, super-cooled or otherwise energized catheter tips ablate the section of tissue responsible for the cardiac arrhythmia.

One such method for treating disorders associated with the conduction of electrical signals in cardiac tissue is described in U.S. Pat. No. 4,641,649. There, an antenna located at the distal tip of the catheter receives electrical signals from the heart which aids the physician in determining the source of the cardiac disorder. Once the source has been located, radiofrequency or microwave frequency energy is applied to the section of tissue through the tip of the catheter to ablate the source of the electrical disorder. The ablation can be controlled by means of an attenuator which regulates the amount of power radiated by the antenna.

Another example of a method and apparatus for ablating a portion of body tissue is described in U.S. Pat. No. 5,147,355. There, a catheter is guided through the patient's body to the area of tissue to be ablated. An electrode located at the catheter tip monitors electrical activity of the tissue and transmits the information to a monitor display. After the physician has positioned the tip of the catheter at the suspected source of the arrhythmia, the tip of the catheter is cryogenically super-cooled to ablate the desired section of heart tissue. The device in this patent includes a flow control valve to regulate the amount of cryogenic liquid delivered to the catheter tip, and thereby try to control the temperature and rate of tip cooling. It is unclear from the description in U.S. Pat. No. 5,147,355 how or whether the operator is able to determine the tip temperature. If during the course of cryoablation, an arrhythmic signal continues to be detected by the electrode, the cryoablation may be curtailed and the catheter tip repositioned to cryoablate another section of tissue suspected of being the source of the arrhythmia.

The catheter described in U.S. Pat. No. 5,147,355 includes first and second concentric fluid flow passages adjacent the tip portion for the flow of cryogenic fluid. Accordingly, the flow passages of the catheter must be made of a rigid material such as stainless steel or other material capable of withstanding the high pressures and temperatures as low as −60° C. associated with liquid-to-gas phase change in a cryogenic fluid. As a result, the catheter is necessarily less flexible and more difficult to maneuver than is desirable when advancing the catheter through the vascular system of a patient.

One of the drawbacks with the above-described method for treating cardiac arrhythmia is that it does not allow for precise control of the probe tip temperature. For example, in the cryoablation method described in U.S. Pat. No. 5,147,355, the temperature of the catheter tip is regulated by the amount of cryogenic fluid delivered to the catheter tip. Using this method, change in the temperature of the probe tip is gradual, and rapid and precise temperature adjustment to the probe tip over a broad range of temperatures is difficult to achieve. The inability to quickly adjust the probe tip temperature may result in some destruction of sections of heart tissue that are not responsible for the arrhythmia.

Although it is known that cooling the heart tissue can cause observable changes in the electrical activity of the heart Hariman et al., "Cryothermal Mapping of the Sinus Node in Dogs: A Simple Method of Localizing Dominant and Latent Pacemakers," *Cardiovascular Research*, 1989, Vol. 23, pp. 231–238 and Gessman, "Localization and Mechanism of Ventricular Tachycardia by Ice-Mapping 1-Week After the Onset of Myocardial Infarction in Dogs," *Circulation*, Vol. 68, No. 3, September 1983, pp. 657–666, which are incorporated by reference herein, the present methods for treating arrhythmia, as described above, typically have not utilized cooling of the heart tissue for purposes of identifying the foci of the aberrant signals, but have used low-temperature cooling for ablation.

SUMMARY DISCLOSURE OF THE INVENTION

The present invention is generally directed to methods and apparatus for use in procedures related to the electrophysiology of the heart, such as identifying or evaluating the electrical activity of the heart, or diagnosing and/or treating conditions associated with the electrophysiology of the heart. In accordance with one aspect of the present invention, the apparatus includes an elongated body having proximal and distal end portions. The distal end portion includes at least a first electrode and a second electrode proximally spaced from the first electrode. One or more pairs of thermocouple elements or "legs" are located between the electrodes. One end of one of the thermocouple elements is conductively connected to one end of the other thermocouple element at a junction. The temperature of the junction may be affected by applying a voltage across the thermocouple elements in accordance with the Peltier effect.

In accordance with another aspect of the present invention, a probe for use in cardiac-related procedures is also provided. The probe includes a carrier having low thermal and electrical conductivity and at least two thermocouple elements conductively connected at a junction and mounted on the carrier. The probe also includes at least one electrode.

In accordance with another aspect of the present invention, a method is provided wherein an apparatus having thermocouple elements of different electromotive potentials, which are conductively connected at a junction is introduced into the interior of the heart. The junction is brought into contact with a section of the heart tissue. An electrical current is passed through the thermocouple elements to reduce the temperature of the junction in accordance with the Peltier effect, and thereby cool the heart tissue without damaging the heart tissue. The heart is monitored for any effect of the cooling (by, for example, direct observation by a physician or by sensing or recording by a machine). After cooling, the temperature of the heart tissue is returned to normal, such as by actually warming the heart tissue or by allowing the heart tissue to warm on its own.

Finally, in accordance with another aspect of the present invention, a method for treating heart arrhythmia is also provided. As in the method referred to above, an apparatus having thermocouple elements of different electromotive potentials conductively connected at a junction is introduced into the interior of the heart, and a section of heart tissue is contacted with the junction. The junction is cooled by passing an electrical current through the thermocouple elements in accordance with the Peltier effect, and thereby cool the heart tissue without damaging the heart tissue. The heart may be monitored for an effect of such cooling. By monitoring for the effect of the cooling on the electrophysiology of the heart, the physician is able to determine whether or not the source of the arrhythmia has been located. If it is determined that the source of the arrhythmia has been correctly identified, the section of tissue may be immediately treated, for example, by ablating the desired area while the junction is still in contact with the section of heart tissue, so as to substantially permanently interrupt the source of the arrhythmia.

DESCRIPTION OF THE DRAWINGS

FIG 3 is a plan view of the apparatus embodying the present invention;

FIG. 4 is a longitudinal cross-sectional view of the distal end of the apparatus of FIG. 3;

FIG. 5 is a transverse cross-sectional view taken through 5—5 of the distal end of FIG. 4;

FIG. 6 is a more detailed elevational view of the distal end of the apparatus of FIG. 3;

FIG. 7 is a plan view of another embodiment embodying the apparatus of the present invention;

FIG. 8 is a longitudinal cross-sectional view of the distal end of the apparatus FIG. 7;

FIG. 9 is a transverse cross-sectional view taken through 9—9 of the distal end of FIG. 8;

FIG. 10 is a more detailed elevational view of the distal end of the apparatus of FIG. 7;

DETAILED DESCRIPTION OF THE DRAWINGS

Figure 1:
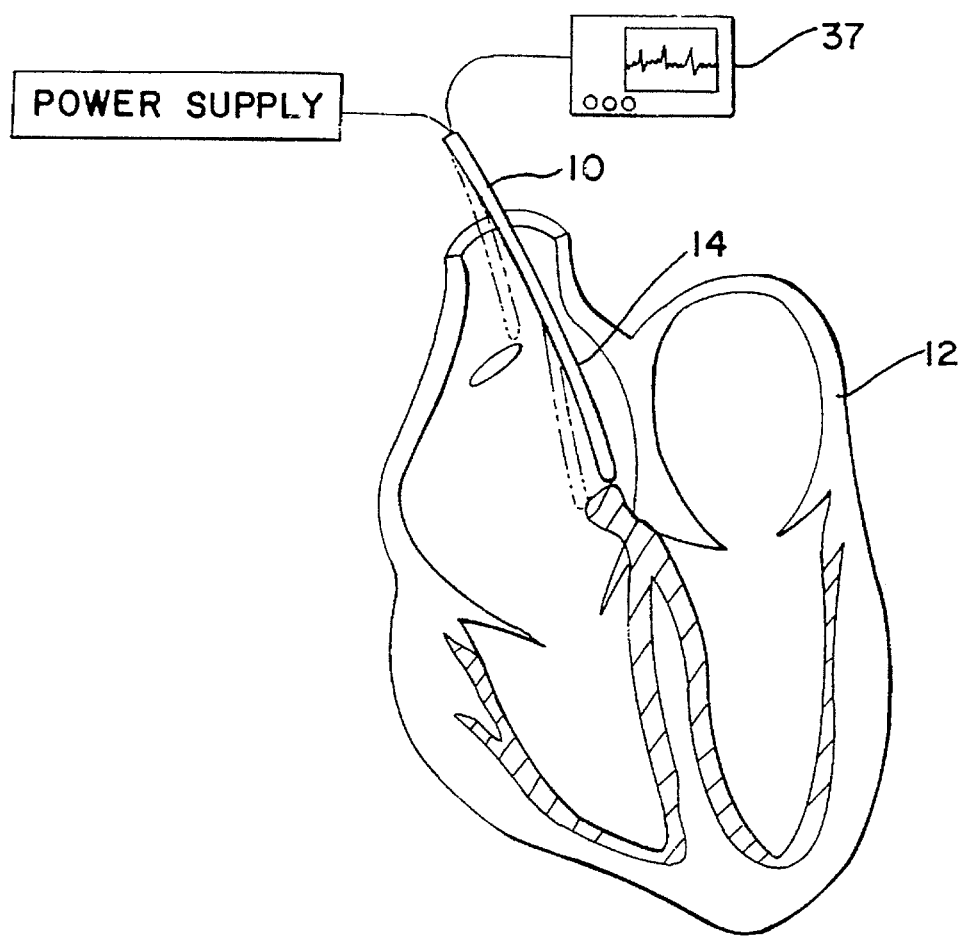
FIG. 1 is a cross-sectional view of a human heart with the apparatus embodying the present invention disposed within the heart at different locations.

Turning now to the drawings, FIG. 1 shows a distal end portion of an elongated catheter 10, as it may be used in accordance with the present invention, disposed within a human heart 12. More particularly, the distal end portion includes a catheter probe 14 in contact with a selected area of heart tissue. Herein, the term "probe" refers to an apparatus located at the distal end portion of the catheter that includes the thermocouple elements of different electromotive potential, as described in more detail below. As used herein, the term "catheter" is intended to refer to the entire catheter apparatus from proximal to distal ends, and including the "probe."

Figure 2:
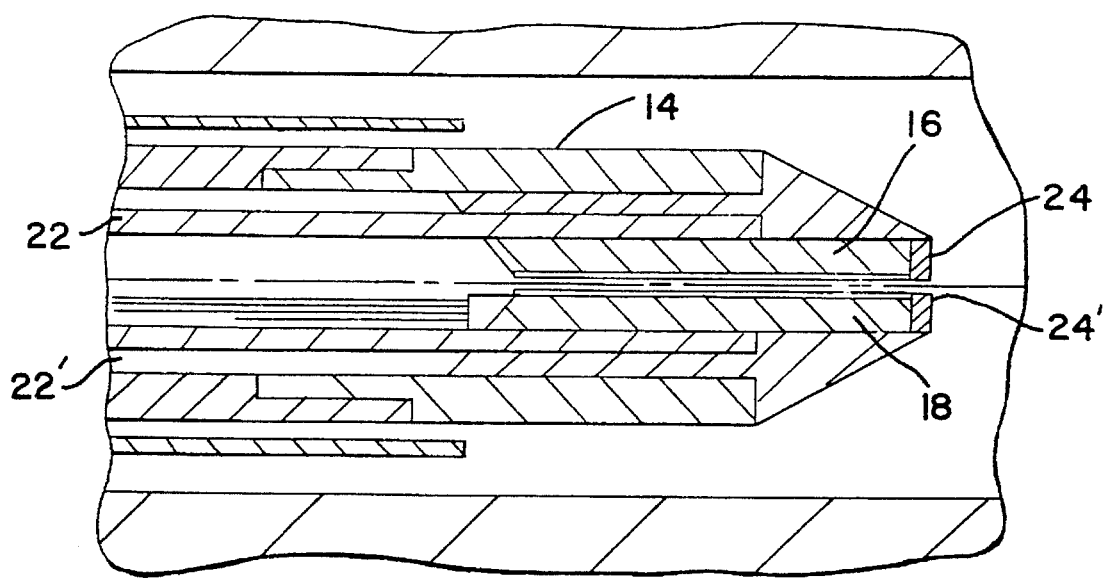
FIG. 2 is a longitudinal cross-sectional view of the distal end portion of an apparatus utilizing the Peltier effect.

The probe 14 employed in the catheter 10 incorporates a thermocouple generally of the type described in U.S. Pat. No. 4,860,744. As set forth in that patent, such thermocouples may comprise two elements or "legs" of differing materials having a large difference in electromotive potential (i.e., different Seebeck coefficients). The difference in electromotive potential between the two elements or "legs" is achieved by doping the elements to produce either positive (P-type) or negative (N-type) elements. The two elements are conductively joined at one end to form a junction. When current flows through the elements, one end of each thermocouple element is cooled while the other end of each thermocouple element is heated. The direction of the current determines which end is cooled and which is heated. This phenomenon is known as the Peltier effect. A detailed description of the Peltier effect and a probe 14 (shown in FIG. 2) utilizing the Peltier effect is set forth in U.S. Pat. No. 4,860,744 titled "Thermoelectrically Controlled Heat Medical Catheter" which is incorporated by reference herein.

As described in U.S. Pat. No. 4,860,744 and generally shown in FIG. 2 of the present application, probe 14 utilizes a single thermocouple design sometimes referred to as a unicouple. The unicouple utilizes one pair of P and N thermocouple elements or legs. The P leg 16 and N leg 18 are electrically separated along their lengths, but are conductively joined at one end. These ends of the thermocouple are referred to as junctions 24, 24'. The P and N legs 16, 18 are separately connected to connector wires 20 20' through which electrical current is fed. In general, thermoelectric heating of junctions 24, 24' occurs when an electrical current is passed through the couple in the P to N direction. When the direction of the current is reversed, by reversing the voltage, the tip of probe 14 is cooled in accordance with the above-described Peltier effect.

It should be noted that the above-identified patent is particularly directed to the use of the Peltier effect for heating a probe tip to melt or vaporize deposits in a patient's body such as atheromatous plaque—an application very different from that claimed herein.

One embodiment of the apparatus of the present invention is shown in FIG. 3. More particularly, FIG. 3 shows a catheter 40 for cardiac-related procedures such as identifying or evaluating the electrical activity of the heart (by, for example, mapping), identifying an electrophysiological source of heart arrhythmia and/or treating heart arrhythmia.

Catheter 40 comprises an elongated hollow tube constructed of any suitable, biocompatible material. The material used for the catheter should be flexible so that the catheter may be easily guided through the vascular system of the patient. An example of such a material is polyurethane. Braiding or other stiffening material may be used in accordance with known techniques, as desired, to allow improved control of the catheter or to permit insertion of the catheter without the use of a guiding device.

As shown in FIG. 3, catheter 40 includes a proximal end portion 42 and a distal end portion 43. Distal end portion 43 of catheter 40 includes a probe portion or "probe" 44 for contacting the heart tissue. To assist in the positioning of the probe 44 within the interior of the heart, a steering wire 46 may be provided, which extends through the catheter 40 essentially between distal end portion 43 (at or near the probe) and a slidable hub 48 located near or within the proximal portion 42. As seen in FIG. 3, sliding hub 48 causes the distal end portion 43 (and the probe 44) of catheter 40 to bend. This may assist in guiding the probe to the desired location and bringing the probe 44 into contact with the surface of the heart tissue. Once the probe 44 has been positioned at or near the desired location of the heart tissue, the electrical activity of the heart may be identified, evaluated or mapped, and electrophysiological sources of arrhythmia may be identified and/or treated.

As shown in FIGS. 4 and 6, probe 44 includes a thermocouple carrier 47, for retaining and supporting the heating and cooling elements described below. In general, thermocouple carrier comprises a molded body, approximately 10 mm in length, for supporting thermocouple elements or "legs" 48 and 50. The thermocouple carrier should be made of a rigid material that is relatively easy to machine and/or mold. Furthermore, the material used for the thermocouple carrier should have low thermal conductivity and low electrical conductivity. One such suitable material is a polyether ether ketone (PEEK).

Figure 16:
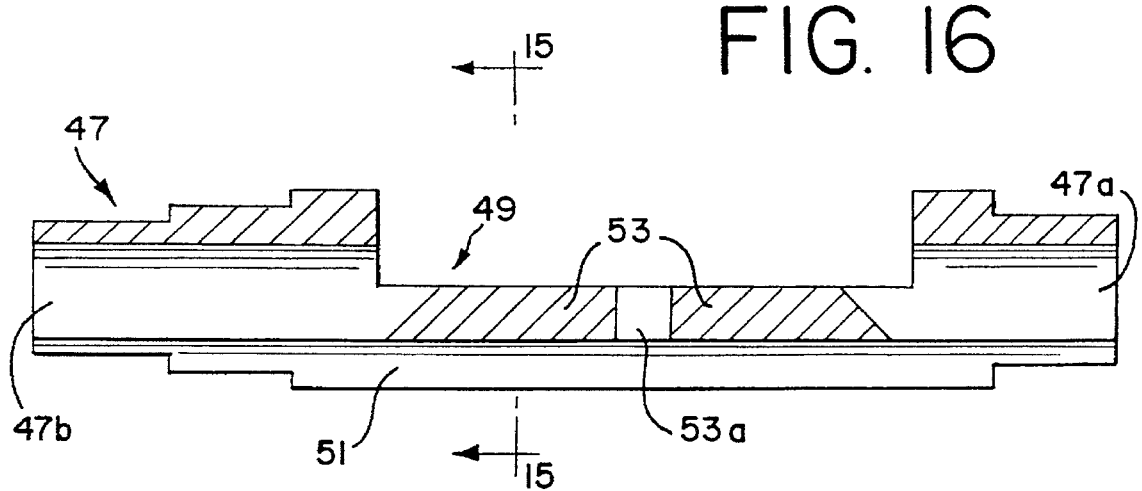
FIG. 16 is a longitudinal cross-sectional view of an alternative embodiment of a thermocouple carrier that may be used in the present invention.
Figure 17:
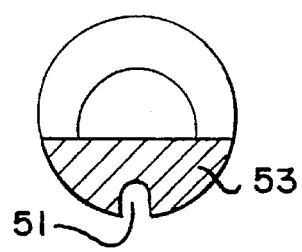
FIG. 17 is a transverse cross-sectional view, taken through 17—17 of the thermocouple carrier of FIG. 16.

The thermocouple carrier 47 of FIGS. 4 and 6 is shown without thermocouple elements 48 and 50 in FIGS. 16 and 17. As seen in FIG. 16, thermocouple carrier 47 is generally cylindrical and includes distal bore 47a, proximal bore 47b and recessed area 49 between the bores for receiving thermocouple elements 48 and 50. A groove 51 below recessed area 49 forms an off-center passageway, which provides a conduit for the different wires and sensors used in the probe. (These wires and sensors are described in more detail below.) Wall portion 53 separates and insulates groove 51 (and the wires that typically extend therethrough) from recessed area 49 (and the thermocouple elements typically disposed therein). An opening 53a in wall portion provides a conduit (for a temperature sensor described below) between recessed area 49 and groove 51. The location of the wires within the thermocouple carrier 47 relative to the thermocouple elements is more clearly seen in FIG. 4.

As shown in FIG. 4, thermocouple elements or legs 48 and 50 are positioned within thermocouple carrier 47 in a longitudinally extending end-to-end arrangement (i.e. the thermocouple element 50 being positioned in a more distal location relative to the other thermocouple element 48). Both of the thermocouple elements 48 and 50 are connected at their ends to a power supply (as generally shown in FIG. 1) via connecting wires 52 and 54 for applying a voltage and inducing current through the thermocouple elements 48 and 50. Typically, connecting wires 52 and 54 are soldered to the thermocouple elements 48 and 50, although other attachment means also may be used. The other ends of thermocouple elements 48 and 50 are joined to form a junction 56 which may be cooled or heated depending on the direction of the current and in accordance with the above-described Peltier effect. As shown in FIGS. 4 and 6, in the preferred embodiment, junction 56 is spaced from the very tip of probe 44. Placement of junction 56 at a location spaced from the probe tip (i.e., on the "side" of probe 44) makes it easier to position and maintain the probe in contact with the pulsating heart.

Thermoelectric cooling of the junction 56, occurs when an electrical current is passed from a power supply through wires 52 and 54 to thermocouple elements 48 and 50. When the direction of the current is reversed by reversing the voltage in the power supply, the junction 56 is heated. Thus, by controlling the voltage of the power supply and the current through thermocouple elements, one can effectively and quickly control and adjust the temperature of junction 56.

As cooling or heating of junction 56 is achieved by introducing a current through the thermocouple elements 48 and 50 in a specific direction, it is desirable that the thermocouple elements be made of a material that can be quickly and efficiently cooled and/or heated. Although several different materials may be used, preferably the thermocouple elements are made of alloys including Bismuth-Telluride (Bi—Te). The thermocouple elements may include other materials or be appropriately doped (as described in U.S. Pat. No. 4,860,744) to produce a P-type element and an N-type element. For example, in the present invention, the p-type element may include 72% Antimony Telluride ($Sb_2Te_3$), 25% Bismuth Telluride ($Bi_2Te_3$) and 3% Antimony Selenide ($Sb_2Se_3$) doped with excess Tellurium (Te). The n-type element may include 90% ($Bi_2Te_3$), 5% ($Sb_2Se_3$) and 5% ($Sb_2Te_3$) doped with Antimony Triodide ($Sb\ I_3$).

The wires that connect the thermocouple elements 48 and 50 to the power supply should be flexible, having a low electrical resistance and a large surface area for heat transport such as, for example, a Litz wire available from Kerrigan Lewis Manufacturing Co. of Chicago, Ill. (part or product no. 210/48). Junction 56 is preferably formed by soldering the ends of thermocouple elements 48 and 50 with an organic solder that has a high melting point, high thermal conductivity and has a high degree of electrical conductivity. An example of such an organic solder is part or product no. 5N60PB4066 available from Kester Solder Co. of Des Plaines, Ill.

Gaps between the ends of elements 48 and 50 and the carrier are preferably filled with a thermally conductive epoxy 57. The epoxy 57 may be finished to provide a smooth exterior surface for the probe. The epoxy also assists in drawing heat from the hot ends of the thermocouple elements, thereby assisting in maintaining the cool ends of the thermocouple elements at the desired temperature. One such epoxy believed to be suitable is Oxy Cast made by Resin Technology of Easton, Mass.

Precise temperature control of the junction 56 may be achieved by precalibration of the power supply so that the temperature achieved by a given current flow is accurately known. Alternatively, the temperature of the junction 56 may be actually monitored. Various devices for monitoring the temperature of junction 56 may be used without departing from the present invention. In the illustrated embodiment the temperature of junction 56 may be measured and monitored by a temperature sensor 58 which is embedded in the solder junction 56. Temperature sensor 58 extends from junction 56, through opening 53a, groove 51 and proximal bore 47b of thermocouple carrier 47, through the body of catheter 40 and is attached to a standard temperature monitoring display (not shown). In this embodiment, the temperature sensor 58 may be made of an iron/constantan material that is "TEFLON" (polytetrafluoroethylene) insulated and has a diameter of about 1.1 mm (0.005 inches). The length of temperature sensor will naturally depend on the length of the probe and catheter. Such a sensor is available from OMEGA Engineering of Stanford, Conn. and sold as product or part no. 5SC-TT-J-36-72. Alternatively, a thermocouple thermometer may be used to monitor the temperature of the junction. Still other means for monitoring the temperature of the probe 40 are set forth in U.S. Pat. No. 4,860,744, and in U.S. Pat. No. 5,122,137, assigned to Boston Scientific and also incorporated by reference.

In addition, as shown in FIGS. 4 and 6, probe 44 also includes spaced electrodes 62 and 64 for monitoring the electrical signals in the heart tissue. By monitoring the electrical signals in the heart, the electrodes assist in identifying the location of the heart arrhythmia or damaged heart tissue. The distal electrode 62, shown in FIGS. 4 and 5, is located at the tip of the probe 44. Distal electrode may be made of stainless steel (such as SS316) or any other suitable electrically conductive and biocompatible material. Proximal electrode 64, shown in FIGS. 4 and 6, is approximately 1.5 mm in length and is also made of an electrically conductive and biocompatible material. Distal and proximal electrodes 62 and 64 are preferably spaced equal distances from junction 56.

As shown in FIG. 4, distal electrode 62 is connected to a monitoring device 37 (as generally depicted in FIG. 1) such as an ECG by wire 65 which is soldered or otherwise connected to the distal electrode 62 and extends through passageway 49 of thermocouple carrier 47. Proximal electrode 64 is also connected by a soldered wire (not shown) to a monitoring device 37. The wires that connect the distal and proximal electrodes to the monitoring device 37 should be of a flexible material having a small diameter and a low electrical resistance. A wire believed to be suitable in this and the other embodiments described herein is a copper wire, 36 AWG with polyamide insulation, available from Mid-West Wire Specialties Co. of Chicago, Ill.

Turning now to FIG. 7, another embodiment of the apparatus of the present invention is shown. In particular, FIG. 7 shows an apparatus such as catheter 66 which may be used for cardiac-related procedures such as evaluating (by, for example, mapping) the electrical activity of the heart, identifying the source of heart arrhythmia and/or treating heart arrhythmia. Catheter 66 has a hollow body portion and is made of a suitable, flexible, biocompatible material such as polyurethane. As seen in FIG. 7, catheter 66 includes a proximal portion 67 and a distal end portion 68. Distal end portion 68 includes a probe portion or "probe" 69 for contacting the heart tissue. Directional control of the probe may be achieved by steering wire 70 in the manner previously described.

Figure 15:
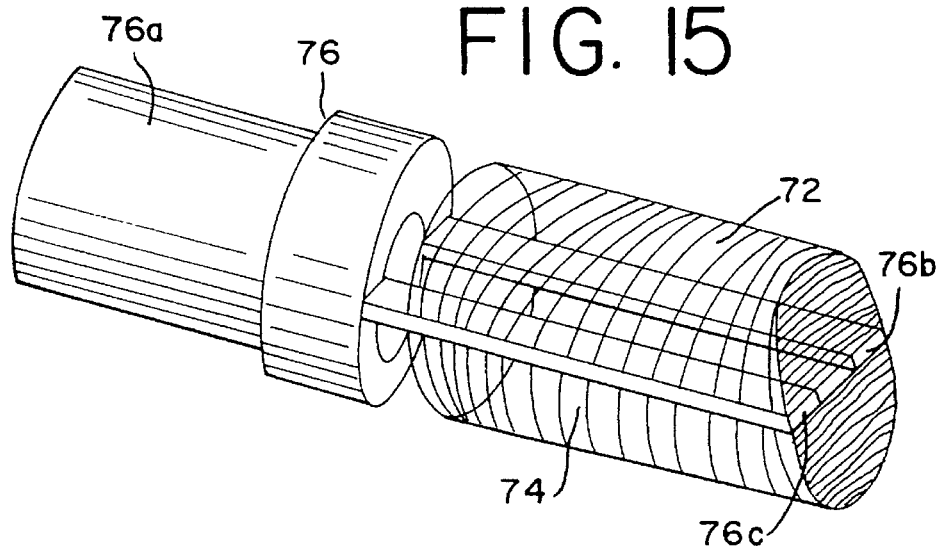
FIG. 15 is a plan view of an embodiment of a thermocouple carrier that may be used in the present invention.

A general view of the probe 69 is seen in FIG. 10 and a more detailed cross-sectional view of probe 69 is shown in FIG. 8. As seen in FIG. 8, thermocouple elements or legs 72 and 74 are arranged on thermocouple carrier 76 in a parallel or "side-by-side" arrangement. A more detailed view of thermocouple carrier 76 is shown in FIG. 15. As seen in FIG. 15, thermocouple carrier 76 includes a hollow body portion 76a and two thin, elongated, spaced apart support members 76b and 76c extending between and supporting the thermocouple elements 72 and 74 in a spaced apart relationship. Referring back to FIG. 8, wires 78 and 80 are connected (as by soldering) to the proximal ends of thermocouple elements 72 and 74 and extend through the hollow body portion 76a of thermocouple carrier 76 and through the body of probe 69 and catheter 66 (as seen in FIG. 8) to a power supply (shown generally in FIG. 1). The distal ends of thermocouple elements 72 and 74 are soldered to distal electrode 82 to form a "junction" between the elements of the thermocouple. In this manner, distal electrode/junction 82 may be cooled or heated by applying a voltage across the thermocouple elements 72 and 74 to induce an electrical current through thermocouple elements 72 and 74.

As described above in connection with the earlier embodiment, thermocouple elements 72 and 74 should be made of a material that can be quickly and efficiently cooled (e.g. Bi—Te). In addition, thermocouple elements may include other materials or be appropriately doped to provide a P-type element and an N-type element as discussed above in connection with the embodiment of FIGS. 3–6. Wires 78 and 80 should be flexible, have a low electrical resistance and a large surface area for heat transport such as, for example, the above-described Litz wire.

A thermoconductive epoxy 83 of the type described above may be used to fill the gaps between the proximal ends of the thermocouple elements 72, 74 and body portion 76a of thermocouple carrier to form a smooth continuous outer surface of probe 69. In addition, epoxy 83 draws heat from the ends of the thermocouple elements and, thereby, assists in keeping the other ends of elements 72 and 74 cool.

Referring still to FIG. 8, a temperature sensor 84 extends through the body of catheter 66 and through probe 69 between thermocouple elements 72 and 74, where it is preferably embedded in the solder used to conductively connect the thermocouple elements 72 and 74 to the distal electrode 82.

In addition to distal electrode/junction 82, probe 69 also includes a proximal electrode 86. Like distal electrode 82, the proximal electrode assists in locating the diseased heart tissue. The proximal electrode can also serve as a backup for the distal electrode/junction 82 if, for example, the electrode function of the distal electrode/junction 82 is adversely affected by the conductivity of the attached thermocouple elements. Finally, proximal electrode 86 may be used to ground the system.

Distal electrode/junction 82 and proximal electrode 86 are connected to a monitor, such as an ECG, (shown in FIG. 1) which records the amplitudes of the electrical signals detected by the electrodes 82 and 86. More specifically, proximal electrode 86 is connected to the monitor via wire 88. Distal electrode/junction 82 transmits electrical signals through wires 78 and/or 80 to the monitor via a switching device (not shown) for establishing an electrical connection between wires 78 and/or 80 and the monitoring device. Alternatively, wires 78 and/or 80 may be detached from the power supply and connected to the monitoring device. As in the earlier embodiment, electrodes 82 and 86 should be of an electrically conductive and biocompatible material. In the present embodiment, for example, distal electrode 82 comprises a silver cap. Wire 88 should be flexible, have a small diameter and have a low resistance.

Figure 11:
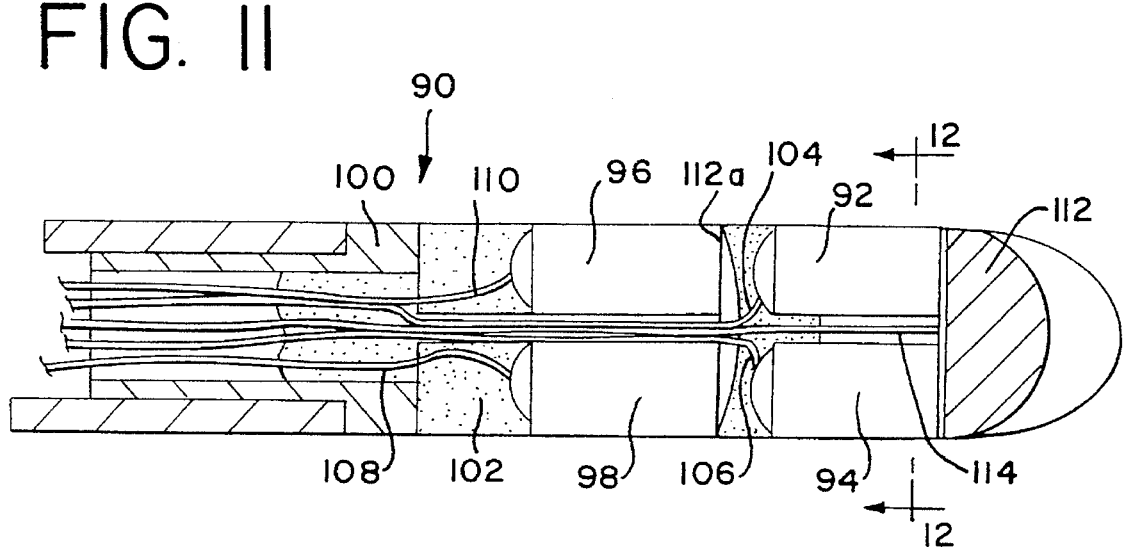
FIG. 11 is a longitudinal cross-sectional view of another embodiment of the distal end of an apparatus embodying the present invention.
Figure 12:
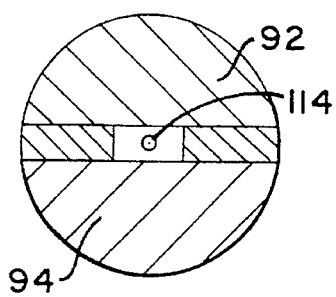
FIG. 12 is a transverse cross-sectional view taken through 11—11 of the apparatus of FIG. 11.

Still another embodiment of the present invention and, in particular of, a probe is shown in FIGS. 11–12. As seen, for example, in FIG. 11, probe 90 includes two sets of thermocouple elements and utilizes a "two stage cooling process." More specifically, probe 90 includes a primary set of two thermocouple elements 92 and 94 (i.e. located near the distal tip of probe 90) and a secondary set of two thermocouple elements 96 and 98 spaced from elements 92 and 94. Both sets of thermocouple elements are supported by thermocouple carrier 100 similar to the thermocouple carrier shown in FIG. 8. The thermocouple elements are made of the same material as the elements described above and/or may be doped or otherwise combined with other materials to provide P-type and N-type elements.

A thermoconductive epoxy 102 may be used to fill the gaps between the primary and secondary sets of thermocouple elements and the thermocouple elements and carrier 100. As described above in connection with the other embodiments, epoxy 102 also draws heat from the proximal ends of thermocouple elements 92 and 94 to allow for greater cooling capacity at probe tip. As in the above-described embodiments, the thermocouple elements are connected to a power supply (not shown) via wires 104, 106, 108 and 110 for introducing electrical current to the thermocouple elements. Wires 104, 106, 108 and 110 are preferably Litz wires of the type described above, but can also be any flexible wire having a low electrical resistance and a large surface area for heat transport. Probe 90 also includes a distal electrode (and junction) 112 and a proximal electrode (not shown). As described above the electrodes are connected to a monitor which records the amplitudes of the electrical signals of the heart tissue.

Cooling of the probe 90 occurs at the distal electrode/junction 112 which is electrically connected (soldered) to thermocouple elements 92 and 94. The secondary set of thermocouple elements 96 and 98 are also conductively connected to form junction 112a. When cooling of the probe is desired, the distal ends of thermocouple elements 92, 94, 96 and 98 and more specifically, junctions 112 and 112a are cooled while the proximal ends of legs 92 and 94 and legs 96 and 98 are heated. Because some heat transfer from the proximal ends of legs 92 and 94 to the distal ends of legs 92 and 94 may occur, complete cooling of distal electrode/junction 112 may not be attained. Accordingly, the cooled junction 112a of the second set extracts heat from the proximal ends of the first set to provide greater cooling capacity at the distal ends of legs 92 and 94. Alternatively, and by the same principle, if the current is reversed, greater heat capacity can be obtained at the distal ends of legs 92 and 94, and, in particular, distal electrode/junction 112. A temperature sensor 114 of the type described above may also be used to monitor the temperature of distal electrode/junction 112. One end of temperature sensor is embedded in the solder used to connect thermocouple elements 92 and 94 to distal electrode/junction 112 and the other end to a temperature monitoring device.

Figure 13:
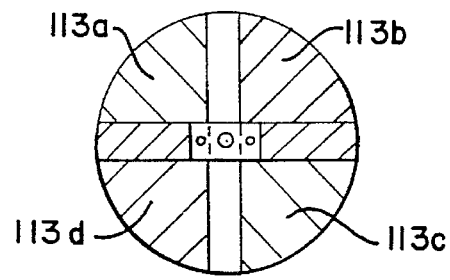
FIG 13 is a transverse cross-sectional view of another embodiment of the distal end of an apparatus-embodying the present invention.

FIG. 13 shows a cross-sectional view of another variant of the two-stage cooling probe similar to the embodiment shown in FIGS. 11–12. In the embodiment of FIG. 13, the primary (distal) thermocouple comprises two thermocouple elements as described above. As seen in FIG. 13 which is a transverse cross-sectional view taken through the secondary set of thermocouple elements, the secondary (proximal) thermocouples comprise two sets of two thermocouple elements 113a,b, c and d. Typically, these thermocouple elements are smaller in size than the thermocouples in the primary set. Element 113a is joined to element 113d at one junction (to form one thermocouple) and elements 113b and 113c are joined at a second junction (to form a second thermocouple). In all other respects, the probe of FIG. 13 is analogous to probe 90 of FIGS. 11–12.

Figure 14:
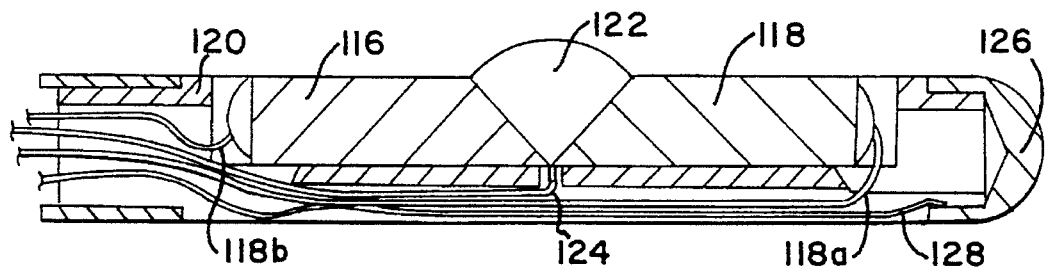
FIG. 14 is longitudinal cross-sectional view of another embodiment embodying the present invention.

Finally, another embodiment of the present invention and, in particular, of a probe, is shown in FIG. 14. This particular embodiment, is essentially the same as described in connection with FIG. 4, except that a heatable tip is provided for use in ablating or treating heart tissue. For example, in FIG. 14, thermocouple elements 116 and 118 are arranged in an end-to-end arrangement within thermocouple carrier 120 with junction 122 formed between thermocouple elements 116 and 118. Elements 116 and 118 are connected, via wires 118b and 118a, to a power supply (shown generally in FIG. 1) for applying a voltage across the thermocouple elements and introducing a current through elements 116 and 118 to cool junction 122. The temperature of junction 122 is monitored by temperature sensor 124. If it is desired to ablate tissue by heating, however, the tip 126 of the probe is heated. As shown in FIG. 14, wire 128 for introducing radio frequency or other ablation energy extends from a power supply to the distal tip 126. In all other respects, the materials used are similar to the materials and method set forth above.

Turning now to the methods of using the foregoing apparatus in carrying out procedures related to the electrophysiology of the heart, such as evaluating (by mapping) the electrical activity of the heart, identifying the electrophysiological source of cardiac arrhythmia and treating the arrhythmia, the catheter (10, 40, 66) is introduced into a patient percutaneously and advanced into proximity with the desired section of the heart 12 (FIG. 1). The present invention is not limited to the means by which the catheter is advanced through the vascular system of the patient. For example, the catheter may be advanced through a guiding or positioning catheter or sheath, or over a guide wire. For in-the-heart the-heart procedures a guiding or positioning catheter may be preferred over a guide wire. In addition to known apparatus and techniques for advancing the catheter through the vascular system of patients, a novel positioning catheter such as the one described in U.S. Ser. No. 08/197,122 filed on Feb. 16, 1994 and assigned to the assignee of the present application may also be used.

As described in more detail below, after the catheter has been sufficiently advanced into the vascular system of the patient, the probe (14, 44, 69, 90) is introduced into the heart interior and brought into contact with the desired section of the heart tissue as generally shown in FIG. 1. More specifically, the junction (24, 56, 82, 112, 122) of the probe is brought into contact with the desired section of tissue. An electrical current is then passed through the thermocouple elements to reduce the temperature of the junction (in accordance with the Peltier effect) and thereby cool the contacted heart tissue. The effect of the cooling on the heart and specifically the effect on the electrical activity of the heart, if any, may be monitored.

The desired section of heart tissue contacted by the probe may be pre-selected by the physician or may be determined based on the presence or absence of electrical activity at that section as detected by the electrodes (62, 64, 82, 86) on the probe and displayed on the ECG 37 or other device.

In accordance with a further aspect of the present invention, the location of the electrical activity in the desired section may be accurately determined.

For example, in the embodiment of FIGS. 3–6, the junction 56 is midway between the electrodes 62 and 64. If the amplitudes of the signals received and transmitted by electrodes 62 and 64 are not substantially equal, this is an indication the sensed electrical activity is not located between the two electrodes. In that case, the probe may be repositioned until the signals are of approximately equal amplitude. Equal amplitudes for the signals being received by the proximal and distal electrodes 64, 62 indicates (to the physician) that the desired section of tissue is located at equal distances between the two electrodes 62 and 64 and, ideally, opposite the location of junction 56 (which, as described above, is also located at equal distances between electrodes 62 and 64). If desired, additional electrodes may also be used to monitor the electrical activity of the heart.

After the junction is placed at the desired section of heart tissue, cooling is achieved by establishing a voltage across the thermocouple elements so as to cause a flow of electric current through the thermocouple elements in order to cool the junction. The temperature of the junction is determined by the directional flow of current (P to N or N to P) as described in U.S. Pat. No. 4,860,744 which has been incorporated by reference. With the junction in contact with the heart tissue, the effect of such cooling on the electrophysiology of the heart, can be observed on the monitoring device 37 (FIG. 1) connected to electrodes.

In the present invention, the junction preferably is cooled to a temperature necessary to affect the electrical activity of the heart at the particular section of tissue without permanently damaging the heart tissue. It is preferred, however, that the junction be cooled to a temperature between −50° C. and 37° C., although any cooling below 27° C. is generally adequate to affect the rate of conduction. In fact, it has been shown that cooling the heart tissue by at least 10° C. can be sufficient to affect and/or suppress the electrical activity of the heart tissue.

Once the junction has been cooled to its desired temperature, contact between the junction and the heart tissue is maintained for, in general, between about 1 second and 15 minutes, depending on the temperature of the junction and the likely depth of the source of the electrical activity within the heart tissue. Electrophysiological changes will also depend on where in the heart the signal is monitored. The contact time will generally be less when the probe and, more specifically, the junction is particularly cold, for example, 20° C. or less and/or when the suspected electrical focus is at a shallow depth within the heart tissue. On the other hand, when the junction is not cooled below about 27° C., the contact time may require several minutes to affect the electrical signal foci that are at a significant depth within the tissue. In either case, the junction is preferably cooled only to the extent necessary to affect the electrical activity without resulting in permanent damage to the heart tissue. A significant benefit of the present invention is that it allows the physician precise and immediate control over the temperature of the probe tip, thereby reducing the risk of unnecessary damage to the heart tissue.

The particular steps which follow the steps described above will vary, depending on the objective of the procedure. If the objective of the procedure is to identify or "map" the electrical activity of the heart, then the probe may be repositioned at different locations of the heart and the above steps of contacting a section of heart tissue with the junction of the probe and cooling the junction and monitoring are repeated.

If the objective of the procedure is to identify the electrophysiological source of heart arrhythmia, the above steps may also be carried out until the source of the arrhythmia is located. If upon cooling of the junction, it is determined that the electrophysiological source of arrhythmia has not been located, the heart tissue may be returned to its normal temperature by terminating the flow of current and allowing the tissue to warm on its own or, for example, by reversing the current (in accordance with the Peltier effect) and warming the heart tissue with the probe. The probe may then be repositioned and the steps of contacting and cooling repeated at the new location.

If the source of the arrhythmia is located and the objective of the procedure is to treat the heart arrhythmia, then the probe may be further cooled or otherwise energized or heated (at, for example, the junction 24, 56, 82, 112 or the tip 126 in FIG. 14). More specifically, the probe is further cooled, energized or heated to treat or ablate the section of heart tissue believed to be the source of the arrhythmia so as to permanently interrupt the aberrant electrical signal.

The precise temperature control provided by the apparatus described above is particularly advantageous in diagnosing and treating arrhythmia. For example, if during cooling of the junction, it is determined that the arrhythmic signal has not been located, cooling of the junction may be quickly terminated by, for example, terminating the flow of current or reversing the flow of current so as to heat the junction. On the other hand, if it is determined that the arrhythmic signal has, in fact, been located, the probe (and specifically the junction) may be immediately energized by, preferably, radio frequency (RF) energy. The radio frequency energy may be introduced from the same power supply used to introduce the Peltier heating but modified to also generate RF waves. Alternatively, a separate power supply for specifically generating the RF waves may be used. Regardless of the source, RF waves are transmitted through wires (e.g. 52 and 54 in FIG. 4 which may be connected to a different power supply) to the thermocouple elements to ablate the contacted tissue. Alternatively, further Peltier cooling or heating, electrical heating, or microwave energy may be used to ablate or otherwise treat the section of tissue at the source of the arrhythmia. For effective ablation, it is preferred that the energized junction (or tip 126 of FIG. 14) be kept in contact with the heart tissue for between about 1 second and 15 minutes to permanently effect treatment.

In sum, in accordance with the present invention, the Peltier effect may used for evaluating, such as by mapping, the electrical activity of heart, identifying the electrophysiological source of arrhythmia and, if desired, ablating a specific area of the heart tissue suspected of being responsible for the arrhythmia. This allows the physician to use the same probe for both identifying the source of arrhythmia and treating it, and permits mapping and ablating in one procedure without removing the catheter from the body of the patient.

Although the present invention has been described in terms of the preferred embodiment as well as other alternative embodiments, various modifications, some immediately apparent, and others apparent only after some study, may be made without departing from the present invention. The scope of the present invention is not to be limited by the detailed description of the preferred embodiment but, rather, is to be defined by the claims appended below.

That which is claimed:

1. A method for evaluating the electrophysiological activity within the interior of a heart comprising:

introducing an apparatus into the interior of the heart, said apparatus having elements of different electromotive potential conductively connected at a junction;

contacting heart tissue within the interior of the heart at a selected location with said junction;

passing an electrical current through said elements to reduce the temperature of said junction in accordance with the Peltier effect and thereby cool the contacted heart tissue without damaging the heart tissue;

monitoring for the effect of the cooling on the heart;

returning the heart tissue at said selected location to a normal temperature.

2. The method of claim 1 comprising reducing said junction to a temperature no lower than about −50° C.

3. The method of claim 1 comprising contacting said selected location of the heart with said junction for between about 1 second and 15 minutes.

4. The method of claim 1 comprising cooling said selected location of the heart by 10° C. to a depth of 8 mm.

5. The method of claim 1 further including repeating the steps of contacting, passing, and monitoring until an electrophysiological source of arrhythmia is located.

6. The method of claim 5 comprising treating said heart tissue at said electrophysiological source of arrhythmia.

7. The method of claim 6 wherein said heart tissue is treated by heating the junction to a temperature sufficient to ablate the selected location of the heart.

8. The method of claim 6 wherein said heart tissue is treated by applying radiofrequency energy thereto.

9. The method of claim 8 comprising applying said radiofrequency energy through said apparatus.

10. The method of claim 6 wherein said heart tissue is treated by applying microwave energy thereto.

11. The method of claim 10 comprising applying said microwave energy through said apparatus.

12. The method of claim 6 comprising contacting said selected location of the heart with said junction for between 1 second and 15 minutes.

13. The method of claim 1 comprising introduced said apparatus through a catheter.

14. A method for treating a source of arrhythmia in a heart comprising:

introducing an apparatus into the interior of the heart said apparatus having elements of different electromotive potential, said elements being conductively connected at a junction;

contacting heart tissue within the interior of the heart at a selected location with the junction;

passing an electrical current through said elements to reduce the temperature of the junction in accordance with the Peltier effect and thereby cool the contacted heart tissue without damaging the heart tissue;

monitoring for the effect of the cooling on the heart to determine whether the source of the arrhythmia has been located;

treating the heart tissue to substantially permanently interrupt said source of arrhythmia.

15. The method of claim 14 wherein said heart tissue is treated by heating the junction to a temperature sufficient to ablate the selected location of the heart.

16. A method of claim 15 comprising contacting said selected location of the heart with said junction for between 1 second and 15 minutes.

17. The method of claim 14 further including the step of returning the heart tissue at said selected location to a normal temperature.

18. The method of claim 14 further including repeating the steps of contacting, passing and monitoring at different locations within the heart until all electrophysiological sources of arrhythmia are located.

19. The method of claim 14 comprising cooling said junction to a temperature no lower than about −50° C.

20. The method of claim 14 comprising contacting said selected location of the heart with said junction for between 1 second and 15 minutes.

21. The method of claim 14 comprising cooling said selected location of the heart 10° C. to a depth of 8 mm.

22. The method of claim 14 wherein said heart tissue is treated by applying radiofrequency energy thereto.

23. The method of claim 22 comprising applying said radiofrequency energy through said apparatus.

24. The method of claim 14 wherein said heart tissue is treated by applying microwave energy thereto.

25. The method of claim 24 comprising applying said microwave energy through said apparatus.

26. The method of claim 14 comprising introducing said apparatus through a catheter.

* * * * *